US00PP13594P29

(12) United States Plant Patent
Trees

(10) Patent No.: US PP13,594 P2
(45) Date of Patent: Feb. 25, 2003

(54) GERANIUM PLANT NAMED 'BALCOLWHIT'

(75) Inventor: Scott C. Trees, Shell Beach, CA (US)

(73) Assignee: Ball FloraPlant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/099,255

(22) Filed: Mar. 15, 2002

(51) Int. Cl.[7] ..... A01H 5/00
(52) U.S. Cl. ..... Plt./332
(58) Field of Search ..... Plt./332

*Primary Examiner*—Kent L. Bell
(74) *Attorney, Agent, or Firm*—C. A. Whealy

(57) ABSTRACT

A new and distinct cultivar of Geranium plant named 'Balcolwhit', characterized by its cascading and mounded growth habit; freely basal branching habit; dark green-colored leaves with a faint zonation pattern; and white semi-double flowers with red purple-colored venation.

1 Drawing Sheet

BOTANICAL CLASSIFICATION/CULTIVAR DESIGNATION

*Pelargonium peltatum* cultivar 'Balcolwhit'.

BACKGROUND OF THE INVENTION

The present invention relates to a new and distinct cultivar of Geranium plant, botanically known as *Pelargonium peltatum*, and hereinafter referred to by the name 'Balcolwhit'.

The new Geranium is a product of a planned breeding program conducted by the Inventor in Arroyo Grande, Calif. The objective of the breeding program was to develop new freely flowering Geraniums with attractive flower and foliage colors.

The new Geranium originated from a cross-pollination made by the Inventor of the *Pelargonium peltatum* cultivar 'Butterfly', not patented, as the female, or seed, parent with the *Pelargonium peltatum* cultivar 'Nicole', disclosed in U.S. Plant Pat. No. 7,358, as the male, or pollen, parent. The cultivar 'Balcolwhit' was discovered and selected by the Inventor as a flowering plant within the progeny from this cross-pollination in a controlled environment in Arroyo Grande, Calif., in 1999.

Asexual reproduction of the new cultivar by terminal cuttings taken at Arroyo Grande, Calif., since June, 2000, has shown that the unique features of this new Geranium are stable and reproduced true to type in successive generations of asexual reproduction.

SUMMARY OF THE INVENTION

The following traits have been repeatedly observed and are determined to be the unique characteristics of 'Balcolwhit'. These characteristics in combination distinguish 'Balcolwhit' as a new and distinct cultivar:

1. Cascading and mounded growth habit.
2. Freely basal branching habit.
3. Dark green-colored leaves with a faint zonation pattern.
4. White-colored semi-double flowers with red purple-colored venation.

Plants of the new Geranium differ from plants of the parents primarily in flower color.

The new Geranium can be compared to the cultivar, 'Balgalsofi', disclosed in U.S. Plant Pat. No. 11,765. However, in side-by-side comparisons conducted in Arroyo Grande, Calif., plants of the new Geranium differed from plants of the cultivar 'Balgalsofi' in the following characteristics:

1. Plants of the new Geranium were larger than plants of the cultivar 'Balgalsofi'.
2. Plants of the new Geranium had smaller leaves with shorter petioles than plants of the cultivar 'Balgalsofi'.
3. Plants of the new Geranium had more petals per flower than plants of the cultivar 'Balgalsofi'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Geranium.

The photograph at the top of the sheet comprises a side perspective view of a typical flowering plant of 'Balcolwhit'.

The photograph at the bottom of the sheet comprises a close-up view of typical flowers of 'Balcolwhit'.

DETAILED BOTANICAL DESCRIPTION

The cultivar 'Balcolwhit' has not been observed under all possible environmental conditions. The phenotype may vary somewhat with variations in environment such as temperature and light intensity, without, however, any variance in genotype. The aforementioned photographs and following observations and measurements describe plants grown 10-cm pots in Arroyo Grande, Calif., under commercial practice in a polycarbonate-covered greenhouse with day temperatures about 20 to 22° C., night temperatures about 18 to 20° C. and light levels about 2,5000 to 3,000 foot-candles. Plants used for the photographs and description were about 8 to 10 weeks from planting rooted cuttings. In the following description, color references are made to The Royal Horticultural Society Colour Chart, 1995 Edition, except where general terms of ordinary dictionary significance are used.

Botanical classification: *Pelargonium peltatum* cultivar 'Balcolwhit'.

Parentage:

*Female parent.*—*Pelargonium peltatum* cultivar 'Butterfly', not patented.

*Male parent.*—*Pelargonium peltatum* cultivar 'Nicole', disclosed in U.S. Plant Pat. No. 7,358.

Propagation:

*Type cutting.*—Terminal cuttings.

*Time to initiate roots.*—About 7 days at 18° C.

*Time to develop roots.*—About 21 days at 18° C.

*Root description.*—Fibrous, freely branching.

Plant description:

*General appearance.*—Cascading and mounded growth habit. Appropriate for 10-cm and larger containers.

*Crop time.*—Starting with a rooted cutting, about 8 to 10 weeks are required to produced a finished flowering plant in 10-cm container.

*Growth and branching habit.*—Vigorous and freely basal branching with about four lateral branches at the base. Pinching, that is, removal of terminal apices, is typically not required.

*Plant height* (*to top of foliage*).—About 12.4 cm.

*Plant width.*—About 36.8 cm.

*Lateral branches.*—Length: About 25.2 cm. Internode length: About 1 cm. Texture: Pubescent. Color: 147C.

*Foliage description.*—Leaves simple, generally symmetrical, abundant, opposite. Quantity of leaves per lateral branch: About 14. Length: About 3.4 cm. Width: About 5.3 cm. Shape: Reniform. Apex: Broadly acute. Base: Cordate. Margin: Palmatifid. Venation pattern: Palmate. Texture, upper and lower surfaces: Leathery; dense pubescence. Color: Young and fully expanded foliage, upper surface: Close to 147A; zonation pattern 187A and located towards the center of leaf; venation, 147C. Young and fully expanded foliage, lower surface: 147B; venation, 147C. Petiole: Length: About 3.6 cm. Diameter: About 2 mm. Color: 147B.

Flower description:

*Flower arrangement and type.*—White-colored flowers with red purple-colored venation arranged in hemispherical umbels arising from apical leaf axils. Umbels displayed above the foliage. At full flowering, usually about eight open umbels and developing umbels per plant. Flowers semi-double and rounded in shape. Umbels persistent. Flowers not fragrant.

*Flowering season.*—Year-round under greenhouse conditions. In the garden, flowering is continuous from spring until fall.

*Umbels.*—Number of flowers per umbel: About six. Diameter: About 7.4 cm. Height: About 4.6 cm. Flower diameter: About 5.2 cm. Flower height (depth): About 1.3 cm.

*Flower buds.*—Length: About 2.1 cm. Diameter: About 9 mm. Shape: Ovoid. Color: Lighter than 56D.

*Petals/petaloids.*—Quantity: About nine petals and about one or two petaloids per flower. Petaloids variable in size and shape. Arrangement: Imbricate. Petal length: Upper petals: About 2.9 cm. Lower petals: About 2.6 cm. Petal width: Upper petals: About 1.9 cm. Lower petals: About 1.7 cm. Petal shape: Obovate. Petal/petaloid apex: Obtuse. Petal/petaloid base: Attenuate. Petal/petaloid margin: Entire. Petal/petaloid texture, upper and lower surfaces: Velvety; glabrous. Petal/petaloid color: When opening and fully opened, upper surface: Upper petals/petaloids: Ground color, 155D; venation, between 71A and 71B. Lower petals/petaloids: Ground color, 155D; venation, 73A, faint. When opening and fully opened, lower surface: Upper petals/petaloids: 155D, random spots, 66A. Lower petals/petaloids: 155D.

*Sepals.*—Quantity: About five, not imbricate. Length: About 1.6 cm. Width: About 5 mm. Shape: Ensiform to lanceolate. Apex: Acute. Margin: Entire. Texture, upper and lower surfaces: Dense pubescence. Color, upper and lower surfaces: 146B.

*Peduncle* (*umbel stem*).—Length: About 4.8 cm. Angle: Erect. Strength: Strong. Texture: Dense pubescence. Color: 146C.

*Pedicel* (*individual flower stem*).—Length: About 2.7 cm. Angle: Erect. Strength: Strong. Texture: Dense pubescence. Color: 147A overlain with 183B.

*Reproductive organs.*—Androecium: Anther quantity: About five. Anther length: About 2 mm. Anther color: Closest to 86B. Pollen amount: Moderate. Pollen color: Between 172A and 171A. Gynoecium: Pistil quantity: One. Pistil length: About 1.5 cm. Stigma shape: Five-parted, star-shaped. Stigma color: Closest to 80A. Style length: About 4 mm. Style color: Closest to 150D.

*Seed/fruit.*—Seed and fruit development has not been observed.

Disease/pest resistance: Resistance to pathogens and pests common to Pelargonium has not been observed.

It is claimed:

1. A new and distinct cultivar of Geranium plant named 'Balcolwhit', as herein illustrated and described.

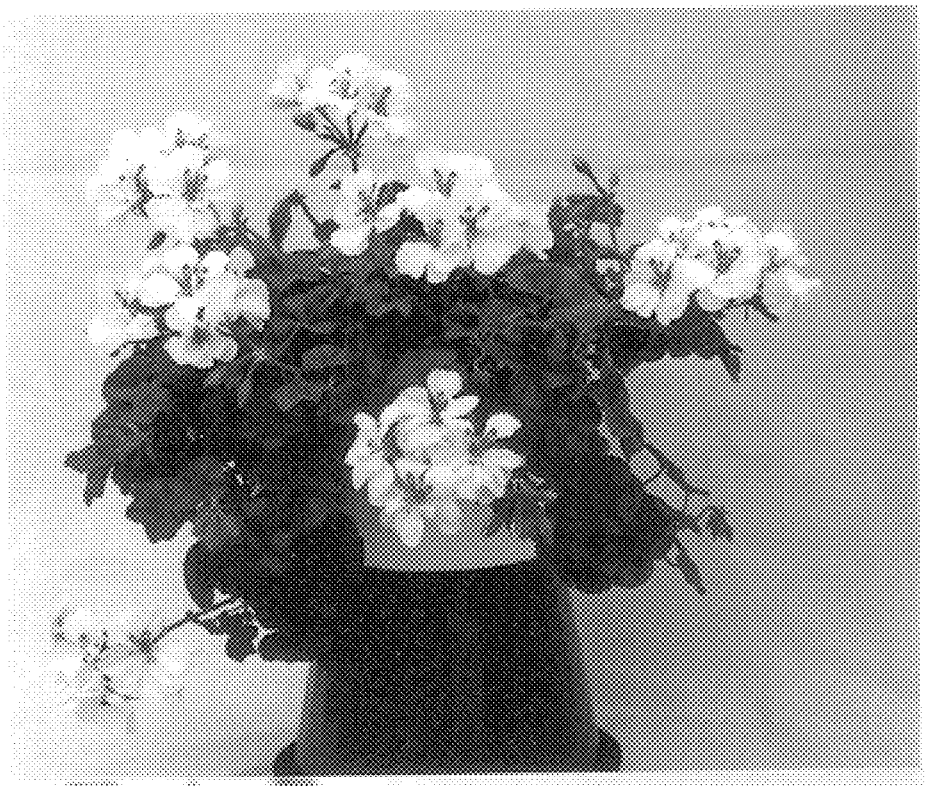
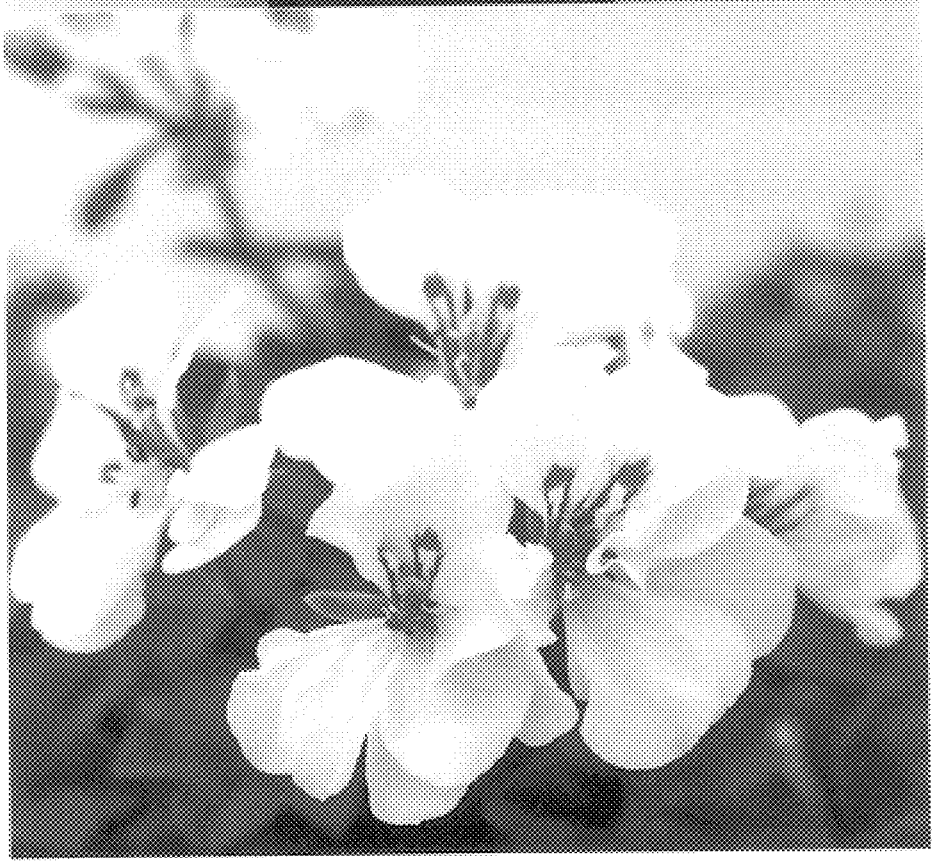

* * * * *